(12) United States Patent
Voltaire (10) Patent No.: US 11,896,369 B2
(45) Date of Patent: Feb. 13, 2024

(54) APTAMER BASED PORTABLE DIAGNOSTIC MEDICAL DEVICE AND METHODS OF USE

(71) Applicant: Ismael Marvin Voltaire, Kissimmee, FL (US)

(72) Inventor: Ismael Marvin Voltaire, Kissimmee, FL (US)

( * ) Notice: Subject to any disclaimer, the term of this patent is extended or adjusted under 35 U.S.C. 154(b) by 957 days.

(21) Appl. No.: 16/699,534

(22) Filed: Nov. 29, 2019

(65) Prior Publication Data

US 2020/0178857 A1  Jun. 11, 2020

Related U.S. Application Data

(60) Provisional application No. 62/834,957, filed on Apr. 16, 2019, provisional application No. 62/772,389, filed on Nov. 28, 2018.

(30) Foreign Application Priority Data

Jan. 28, 2019 (SA) .................................. 119400405

(51) Int. Cl.
*A61B 5/145* (2006.01)
*A61B 5/00* (2006.01)
*A61B 5/1455* (2006.01)

(52) U.S. Cl.
CPC ........ *A61B 5/14514* (2013.01); *A61B 5/0024* (2013.01); *A61B 5/14503* (2013.01); *A61B 5/14546* (2013.01); *A61B 5/14556* (2013.01); *A61B 5/6824* (2013.01); *A61B 5/6828* (2013.01)

(58) Field of Classification Search
CPC ... A61B 5/6833; A61B 5/685; A61B 5/14514; A61B 5/150022; A61B 5/150984; A61B 5/1451; A61B 2562/028; A61B 2562/0285
See application file for complete search history.

(56) References Cited

U.S. PATENT DOCUMENTS

| 7,344,499 B1* | 3/2008 | Prausnitz | A61B 5/150022 600/347 |
| 9,987,427 B1* | 6/2018 | Polsky | A61B 5/150984 |
| 2019/0010499 A1* | 1/2019 | Erickson | C12Q 1/6811 |
| 2019/0231263 A1* | 8/2019 | Ribet | A61B 5/685 |

* cited by examiner

*Primary Examiner* — Eric J Messersmith
(74) *Attorney, Agent, or Firm* — Hunton Andrews Kurth LLP (57) ABSTRACT

The present invention is directed to a cuff-like medical device that may analyze and report the concentrations of various biomarkers in a subject's bodily fluids, samples of which may be extracted by the device in the field and analyzed on the spot using the cuff-like medical device. For example, extracellular fluid (commonly known as "tissue fluid") of a patient may be analyzed by the present invention, and in particular, the constituent interstitial fluid—the known main component of extracellular fluid—may be analyzed for concentrations of one or more specific types of proteins. A sensor component within the device may include one or more aptamers that permit chemical binding of at least one biomarker of interest. When the aptamer-protein binding complex is complete, an electronic component of the device may employ nanoscale weighing using frequency differential analysis through quartz crystal microbalances to determine the presence and concentration of biomarkers.

17 Claims, 7 Drawing Sheets

APTAMER BASED PORTABLE DIAGNOSTIC MEDICAL DEVICE AND METHODS OF USE

CROSS REFERENCE TO RELATED APPLICATIONS

For purposes of establishing priority, reference is made to the following co-pending patent applications: (1) U.S. Provisional Patent Application No. 62/772,389, filed on Nov. 28, 2018; (2) Saudi Arabian Patent Application No. 119400405, filed Jan. 28, 2019; and (3) U.S. Provisional Patent Application No. 62/834,957, filed on Apr. 16, 2019. Each of the foregoing referenced applications is incorporated herein by reference.

BACKGROUND

The availability of detailed biological information, which could aid in triage, on-site patient care, or detailed ongoing medical monitoring is often lacking during remote medical treatment or monitoring performed in-the-field or away from a medical facility. Active or passive monitoring or measurement of, for example, bodily fluids is a well-known process employed by medical laboratories with access to high-tech equipment and specific orders from medical professionals (e.g., doctors) to measure for particular materials that are useful in diagnostics or for similar purposes. However, access to sophisticated laboratories is rarely possible for people in rural/remote locations, or (for example) during unfortunate and unplanned occurrences of a medical traumas. And while modern sports equipment and fitness tracking devices can report steps taken, heartrate, breathing, and other physiological data, they are so far incapable of performing an on-the-spot diagnostic of athletes' bodily fluids to determine levels of fitness, hydration, lack of nutrients, onset of exhaustion, etc. Therefore, and in view of the foregoing, there is a need in the field for a portable medical device capable of providing contemporaneous and on-the-site medical assessment of the patients' bodily fluids to ascertain health status and to render an early and accurate diagnosis, which can immediately or later be used to treat the patient, when access to advanced laboratory equipment in impossible or impractical.

SUMMARY OF THE INVENTION

The present invention is directed to a cuff-like medical device that may analyze and report the amount and concentration of various biomarkers in a subject's bodily fluids, samples of which may be extracted in the field and analyzed on the spot using the device. For example, extracellular fluid (commonly known as "tissue fluid") of a patient may be analyzed by the present invention, and in particular, the constituent interstitial fluid—the known main component of extracellular fluid—may be analyzed for concentrations of one or more specific types of proteins.

In an emergency situation the cuff can be applied to the patient by a paramedic upon arriving at the scene of an accident. A plurality of microneedles, for example, is applied to an interior region of the cuff which might be placed around the forearm or upper leg of the patient. The microneedles are configured to penetrate the epidermis (i.e., the top layer of skin), which lacks nerves and allows for a pain free way to access a patient's bodily fluid. Within minutes, and using the assessment process as detailed herein, the device can provide lab-test-like results in real-time to both the on-scene paramedics and more importantly physicians at the receiving hospital. Continuous monitoring during treatment and observation can serve as an extra layer of protection in case of upcoming health dangers (for example, the device can monitor rising troponin levels which can warn the physician of an impending heart attack). As detailed further below, and as one of skill in the art will appreciate, there are many different situations (apart from an emergency/trauma situation, as described above) where real-time monitoring of constituent components of bodily fluids can be extremely useful or informative for making qualified medical, scientific, or fitness decisions by or on behalf of the device's wearer.

The interstitial fluid is directed from the dermis layer of the patient and into the device for analysis by drawing the fluid through a plurality of microneedles, applied to an interior area of the cuff. The fluid may then continue to pass through a channel within the device and traverse a series of quartz crystals configured in vitro to bond, via aptamer-binding, with the specific molecular structure of one or more elements of interest. The elements may be proteins, biomarkers, nucleic acids, lipids, carbohydrates, or any other element of interest. Although the succeeding disclosure may reference detection of proteins specifically, one of skill in the art will readily appreciate the disclosure to equally pertain to other elements of interest. The aptamers are configured to chemically bind to the molecules of the element desired to be measured (by presence, concentration or otherwise), including by any sub-portion of the molecules of the element of interest. Once the aptamer—protein binding complex is complete, an onboard microprocessor employs nanoscale weighing using frequency differential analysis through quartz crystal microbalances for the purpose of determining the protein concentration within the interstitial fluid.

Accordingly, in one aspect of the disclosed invention, an exemplary wearable device may include: (i) a sample access component; (ii) a sample pre-processing component; and (ii) a sensor component. In a particular such aspect, the sample access component—(i)—may comprise at least one first microneedle, wherein the microneedle is configured to access a biological sample from a subject. In a particular such aspect, the sample pre-processing component comprises at least one first aptamer-based magnetic bead conjugate ("aptamer-MB"), wherein the one first aptamer-MB comprises an aptamer specific for a non-target molecule (i.e., a molecule that is not desired for ultimate diagnostic measuring by the device). In a particular such aspect, the sensor component—(ii)—may comprise at least one first aptamer-based quartz crystal microbalance ("aptamer-QCM"), wherein the one first aptamer-QCM comprises at least a second aptamer specific for one first biomarker. It is further contemplated that the particular components being measured by the sensor component can be selectively chosen and/or interchangeable given a particular situation or desire on the part of the wearer of the device, or the person directing the device to be worn by the wearer for medical/diagnostic purposes.

Implementations of the sensor component can include, but shall not be limited to, one or more of the following features. For example, one or more aptamer-QCM may have two different aptamers specific for the same biomarker. In another example, one or more aptamer-QCM may have two different aptamers specific for two different biomarkers. In yet another example, two or more aptamer-QCM may each comprise a different aptamer specific for the same biomarker.

In yet further aspects, the device may also include (iv) an electronic component. Implementations can include one or more of the following features: a microprocessor, data communication interface, and/or GPS.

In yet other aspects, the device further includes (v) a solution component comprising one or more vials for containing one or more solutions therein. In one such aspect, the solution component comprises a waste vial for storing used buffer and/or processed biological sample solution(s). In another such aspect, the solution component comprises at least one buffer vial comprising a buffer for dissociating molecules from the aptamers associated with the aptamer-QCM, aptamer-MB, and/or aptamer-based filter. In another such aspect, the solution component comprises at least one different buffer vial comprising a buffer for regenerating aptamers associated with the aptamer-QCM, aptamer-MB, and/or aptamer-based filter. In yet another such aspect, the solution component comprises a sample vial for storing at least one fresh biological sample that has been unadulterated by the cuff and collected directly from the patient's bodily fluid(s).

In a further aspect, the device may be housed in a body. In such particular aspects, the body is a cuff configured to fit on an arm or a leg of the subject.

In yet another aspect, each microneedle in the plurality of microneedles may comprise two circular openings on opposing lateral sides of said microneedle. In any of the aspects, the biological sample collected from the subject may be interstitial fluid, however it is contemplated and therefore within the scope of the invention that other bodily fluids known in the art to have medical or scientific value of diagnosis or monitoring may also be included. Although methods of collection will vary, other such bodily fluids (e.g., blood, perspiration, tears, inter-spinal fluid, lymph, breast milk, saliva, urine, bile, lacrimal fluid, peritoneal fluid, etc.). In yet an additional aspect, the biomarkers may be one or more of creatinine, troponin 1, alkaline phosphatase, and/or albumin, however it is contemplated and therefore within the scope of the invention that any biomarker known in the art to have medical or scientific value for diagnosis or monitoring may be further included.

Also provided are provisions to release stored fluids for dilution or cleaning, storage of post-analysis waste, means of communication to remote stations, and methods for mechanical fastening of the device to the patient. Further provided are provisions for collecting pure interstitial fluid for more comprehensive analysis in a separate device. Furthermore provided are methods for monitoring one or more biomarkers in a subject using the device.

The present invention is further directed to a stationary medical device that may be utilized in a dedicated or mobile medical or rehabilitation unit (such as a hospital, fitness center, or ambulance) to analyze bodily fluids (such as interstitial fluid) collected by the cuff-like device in the manner previously described. The stationary medical device may utilize the same aptamer-based system to determine presence of one or more analyzes using quartz crystal microbalance systems, with the distinction that the stationary device is not constrained in size by the wearer's physiology that would otherwise constrain the size/capability of the cuff-like device itself. In other words, the stationary device may be significantly larger than the cuff-like device, enabling it to impart additional redundancy checks to the analyte(s) measured on the more limited cuff-like device to avoid erroneous measurements, as well as to measure for a far greater number of analytes than is physically possible on the cuff-like device. It is contemplated that the stationary medical device may utilize the bodily fluid previously harvested by the cuff-like device. Also similarly to the cuff-like device, the stationary device may utilize buffer solutions, or other known technologies, to dissociate analytes from the aptamers in order to "reset" the aptamers for taking additional measurements. The stationary device may utilize WiFi, GPS, or other connective technologies to impart "smart" monitoring and data analysis for biophysical health information gathered about the subject whose fluid is being analyzed.

The present invention is additionally directed to a removable skin patch (referred to herein as "V-patch") that comprises a removable patch-like structure for placement on a user's skin. The patch-like structure of the V-patch may be fitted with microneedles, similar to the cuff-like device, that are also capable of penetrating the skin up to the depth of the epidermis for the function of drawing out extracellular fluid (such as interstitial fluid). The V-patch will passively collect interstitial fluid in a thin collection chamber on a surface opposed to the microneedle surface. Unlike the cuff-like device, which must be placed on particular regions of the subject (e.g., forearm, leg, etc.) the V-patch is not location-restricted in this manner. The V-patch may be placed on any area of the subject's skin on their body. The V-patch will passively collect interstitial fluid and will automatically stop such collection when the collection chamber is full, or else when the V-patch is removed from the skin. The V-patch may be held in place by temporary adhesive, or other similar mechanism. After removal, the entire V-patch, together with the microneedles and collection chamber, may be inserted into the stationary device, the cuff-like device, or other device, for analysis of the interstitial fluid(s) in the manner previously described. The analysis of fluid collected by the V-patch could take the place of analysis of fluids collected through other means (such as via the cuff-like device), or it could be done in tandem with the other collection methods to double-check or average those previous analyses.

It is contemplated that the disclosed cuff-like device, together or separate from the stationary device and V-patch, may have a vast number of implementations that will facilitate patient care, improve recovery/rehabilitation, monitor chronic conditions, monitor sports fitness characteristics, and other uses. The devices may be utilized by paramedics in a mobile health situation, where a trauma patient must receive medical diagnostics in order to make important health-based decisions regarding patient care. The devices may further/additionally be used in hospitals or dedicated treatment facilities for similar or related diagnostic purposes. The devices may also be used in rehabilitation or recovery facilities to monitor patient healing or recovery from illness or addiction. Other uses may entail performing drug or alcohol testing in mobile situations, including by police or in an ongoing fashion to ensure compliance with court orders. Still further uses may entail use by athletes or fitness training professionals to monitor training progress or athletic performance, where such uses may further enhance an athlete's ability to maximize their athletic performance output by utilizing the diagnostic/data information gathered by the devices to fine-tune hydration, supplementation, heartrate, breathing rate, physical intensity, or duration of activity in order to maximize performance and/or to decrease risk of injury. It is additionally contemplated that, regardless of the type of use, that the device may synchronize with an electronic device (such as a cell phone, personal computer, or other SMART® technology device(s)) such that data and information can be monitored, stored, and interacted with in a user-friendly database. The database may be an App, such as a fitness App, or it might be a medical/healthcare database or system accessible by hospitals, health systems, patients, doctors, pharmacies, health insurance companies, police, courts, etc. All of the foregoing uses, and still others, are contemplated and therefore within the scope of this disclosure.

Variations and modifications can be made to the embodiments of the present disclosure. Other embodiments and aspects of the invention are described in detail herein and are considered a part of the claimed invention. Such other embodiments and aspects can be understood with reference to the following detailed description and accompanying drawings.

DETAILED DESCRIPTION OF THE INVENTION

Figure 1:
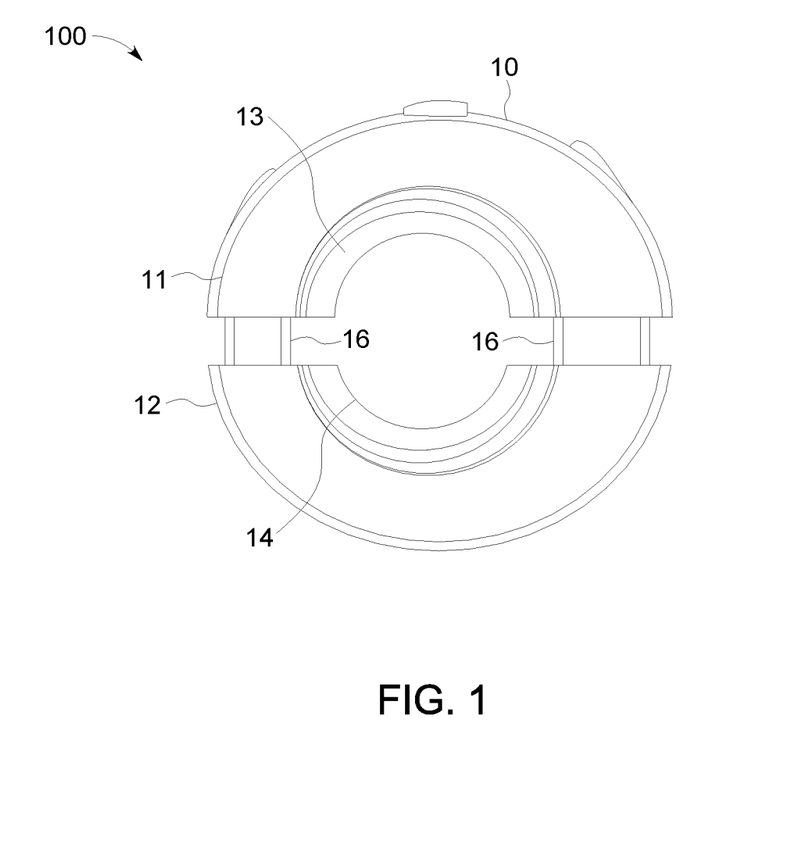
FIG. 1 is a lateral view of an exemplary embodiment of a cuff-like device, shown in an extended position.
Figure 2:
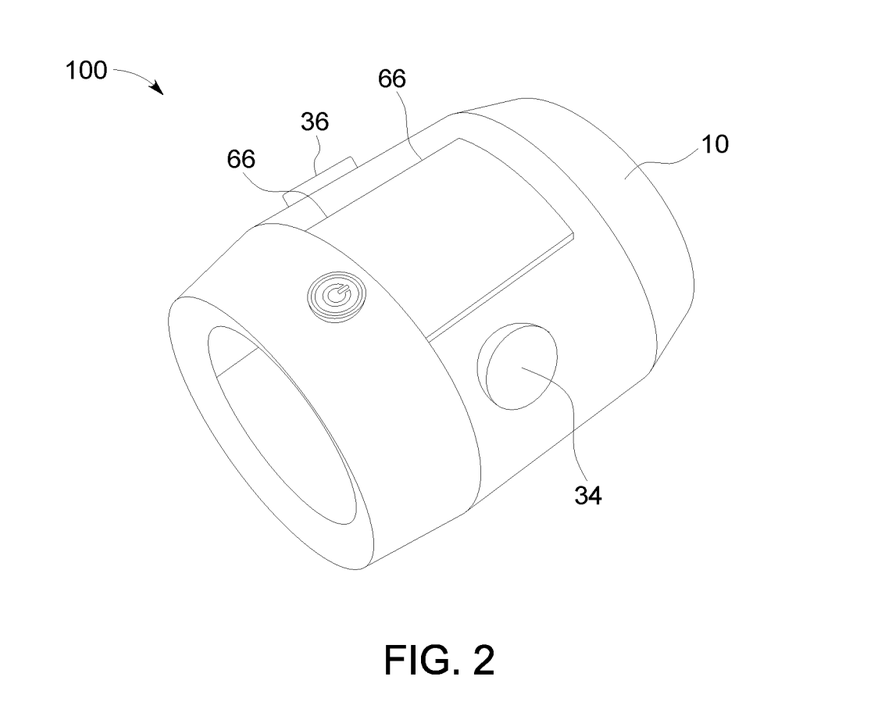
FIG. 2 is an upper isometric view of an embodiment of a cuff-like device, shown in a closed position.

An aspect of the invention is a cuff-like medical device (100), such as a bioassay device illustrated in FIGS. 1-2, that can be worn by an individual and can transdermally extract a sample of bodily fluid (e.g., interstitial fluid) to provide real-time measurement of physiological signatures (e.g., protein concentrations) in order to provide diagnostic or ongoing monitoring capabilities.

Accordingly, an embodiment of the cuff-like device (100) features a device for detecting one or more markers in a sample including: (i) sample access component for obtaining a biological sample from a subject, (ii) a sample pre-processing component for removing non-target molecules from the biological sample, and (iii) a sensor component for measuring the concentration of biomarkers of interest in the biological sample.

In certain embodiments, the device may further include: (iv) a fluidic component, (v) an electronic component, (vi) a solution component, and (vii) a body.

(i) Sample Access Component

In one embodiment, the (i) sample access component includes a needle, lancet, or another suitable puncturing tool as is known in the art for obtaining a biological sample of fluid from a subject. In an embodiment, a plurality of microneedles may be used as the puncturing tool. Microneedles have been shown to be an effective and minimally invasive method for transdermal access for fluid exchange with living subjects. The plurality of microneedles is placed in contact with the patients' skin and acted upon such that the microneedles will penetrate the skin. In one embodiment, the microneedles may penetrate the epidermis at a velocity of 3 meters/second, although other speeds of penetration are contemplated and may be employed.

In an embodiment, a microneedle can have a length, width, height, cross-sectional dimension, circumference, radius (e.g., external or internal radius), or diameter that is less than 1 mm. In an embodiment, the microneedles are between 50 micrometers and 400 micrometers in length. The microneedles should be long enough to consistently penetrate the corneum lucidum where the interstitial fluid is located, but not so long that they might puncture the dermis layer of skin, damaging the nerve endings and causing a modicum of pain to the wearer. The microneedles may be available for use in the device having varying lengths to conform to the unique physiology of the wearer.

Microneedles of various geometry are known in the art. In an embodiment shown in FIG. 6, an exemplary microneedle may be generally conical with a closed point to pierce the epidermis, and two circular openings on each side of the microneedle opening into a single ended hollow base. The dual side openings provide redundancy to reduce the occurrence of needle clogging. When a microneedle is clogged, for whatever reason, it can potentially compromise the uptake of the biological sample by the device. By improving on the existing hollow needle configuration where the opening is placed on the base of the needle, the proposed dual openings will allow continuous flow by a microneedle even in the event that one of the microneedle holes is clogged.

In some embodiments, the microneedles may be composed of a polymer, a metal, silicon, glass, a composite material, or a combination thereof. In a particular such embodiment, the microneedles may be made from silicon. In an embodiment, the width of the microneedle holes can be adjusted in manufacturing to eliminate unwanted molecules from entering the device. In an embodiment, the plurality of microneedles may be removed from the device, sterilized and reused.

In other embodiments, the cuff-like device may employ the use of a small electrical pulse upon application of the microneedles to the epidermis. Such pulse may increase the permeability of the epidermis and thus allow the microneedles to puncture the skin more easily, therefore reducing the chances of irritation with prolonged use. Although pain is generally not observed in the use of microneedles entering the epidermis, the chances of pain are minimized, even more so with the addition of an electrical pulse. The pulse will temporarily cause an increased cell permeability and allows interstitial fluid to be accessed more easily. It is envisioned that such an electrical pulse, where used, may be relatively painless and will permit a decrease in the otherwise-employed speed of puncture for the microneedles (previously disclosed as approximating 3 meters per second) in order to penetrate the epidermis. This decrease in velocity may directly result in a decrease in pain sensation or irritation from prolonged usage of the device. After the needles have penetrated the skin, the cells will generally return to their original state.

In still further embodiments, the microneedles may employ the use of one or more numbing agents as are well known in the art. The use of a numbing agent on the microneedles will further reduce the chances of pain and irritability. The numbing agent can be added during the creation of the microneedles, or it may be applied after manufacturing but before use on the patient. The numbing agent will help avoid irritation of the user and possible distraction. It is contemplated that the numbing agent would be reusable and replaced after the device is used a certain amount of times, or with regular/continued use. In some embodiments, the microneedles may self-secrete the numbing agent before, during, or after the puncturing of the epidermis. The secretion of the numbing agent after puncturing may serve to reduce irritation during long-term use of the device. This could allow users to use the device for prolonged periods of time that may not have previously been possible due to injury or irritation with continual puncture. The amount of the numbing agent may vary with use and patient tolerance so that the numbing effects can wear off shortly after the device is removed from the skin. In some embodiments, the numbing agent may be stored within a separate vial in the cuff-like device. Replenishment of the numbing agent may be done through the attachment of a removable microneedle patch, or by manually adding such numbing agent to the microneedles such as by liquid or gaseous/deposition application methods known in the art. In some embodiments, the cuff-like device may have a numbing agent contained within a vial on the device, similar to the vials that contain buffer solutions or bodily fluid(s), as described herein. In such event the device may periodically utilize the numbing agent from the vial by applying it to the microneedles as described above. In yet still other embodiments of the V-patch, having the above-mentioned capabilities, the numbing agent may be pre-disposed on or within the microneedles.

In yet a further embodiment, the microneedles may further be equipped with a filter near the base of the microneedles, with the filter including a filter mesh that may selectively obstruct certain molecules by size from entering the interior of the device. The filter mesh may be disposable, and may be separately replaced from the microneedles themselves, or alternatively the filter mesh may be one-and-the-same with the microneedles such that they are reusable along with the microneedles or else the filter-microneedle combination is together disposable.

(ii) Sample Pre-Processing Component

For many molecules (e.g., proteins), there are other molecules with similar structure. Accordingly, when assaying for a molecule (e.g., biomarker) of interest, these other molecules with similar structure (herein referred to as "non-target molecule") may be mistakenly assayed, thereby skewing results. Thus, in other embodiments, the (ii) sample pre-processing component may include components for isolation and/or removal of non-target molecules from the biological sample.

Figure 8:
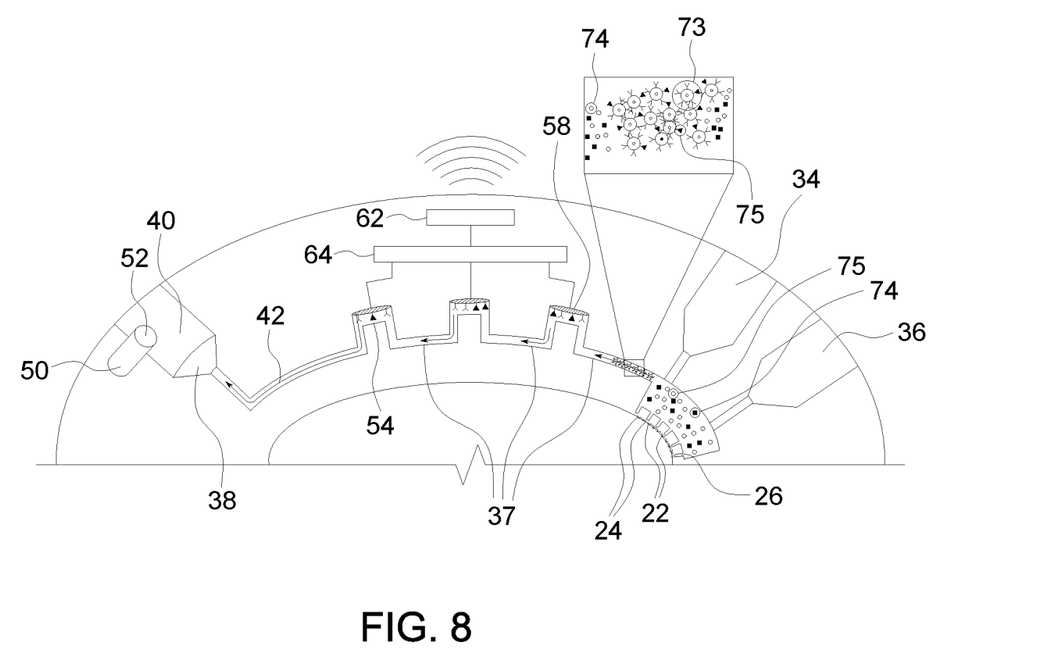
FIG. 8 is a lateral cross-sectional view of a sample pre-processing component, for use with an embodiment of a cuff-like device, the component further including aptamer-magnetic bead conjugates and an aptamer-based filter.

In an embodiment illustrated in FIG. 8, the components of a sample pre-processor may include aptamer-magnetic bead conjugates ("aptamer-MB"), which comprise magnetic beads linked to aptamers. Such aptamer-MB are known in the art (see, for instance, Modh et al. (2018) Sensors 18(4):1041), the disclosure of which is incorporated herein. In some embodiments, the magnetic beads are Invitrogen Dynabeads™ M-450 Tosylactivated (Thermo Fisher Scientific, Waltham, Mass.). In another embodiment, the magnetic beads are Ni-NTA Magnetic Agarose Beads (Qiagen, Hilden, Germany). The aptamer-MB are configured to remove non-target molecules in the biological sample before the biological sample reaches the sensor component. In some embodiments, the aptamers may be removed from the magnetic beads and replaced with other aptamers.

In some embodiments, the sample pre-processing component alternatively or additionally includes a membrane or filter. In some embodiments, the filter will have a pore size that is no larger than the largest biomarker being assessed. In this regard, the filter may remove a plurality of non-target molecules. In an embodiment, the filter is an aptamer-based filter, that is, a filter comprising aptamers in its media. Aptamers in the filter will bind and remove non-target molecules before the biological sample reaches the sensor component. In some embodiments, the aptamers may be removed from the filter and replaced with other aptamers. In another embodiment, the aptamer-based filter will have a pore size that will be no larger than the largest biomarker being assessed.

(iii) Sensor Component

In some embodiments, the (iii) sensor component includes a biosensor for assaying concentration of biomarkers in the biological sample. A biosensor, for example, may comprise monoclonal antibodies in an automated enzyme-linked immunosorbent assays (ELISA) or similar assay. A biosensor may also utilize aptamers, engineered proteins, or peptides to bind to a target biomarker. Adhesion of the target biomarker to the sensor molecule may be measured by, for example, fluorescence (e.g., fluorescence resonance energy transfer (FRET) or fluorescence quenching), surface plasmon resonance (SPR), piezoelectric sensors, SAW sensors, quartz crystal microbalance, or other known biosensor measurement techniques known in the art. In a particular embodiment, the biosensor may be an aptamer-based quartz crystal microbalance ("aptamer-QCM"). The aptamer-QCM comprises an aptamer-based quartz crystal biosensor, that comprises quartz crystals with linked aptamers, and an oscillator circuit coupled to the quartz crystal. Binding of the biomarker of interest to their corresponding aptamers on the quartz crystal produces a detectable resonance via the oscillator circuit in such a way that can be used to determine a change in mass, and by extension used to calculate concentration of the biomarker in the biological sample. In some embodiments, a microprocessor is used to obtain and analyze data from the sensor.

In some embodiments, one or more aptamers may be designated to one or more biomarkers of interest. In an embodiment, two different aptamers will be designated to each of one or more biomarker of interest. In some such embodiments, the two different aptamers designated to a biomarker of interest will be clustered to different sections on the same quartz crystal. In other such embodiments, the two different aptamers will be clustered to different quartz crystals. In some embodiments, the aptamers may be removed from the quartz crystals and replaced with other aptamers.

(iv) Fluidic Component

In some embodiments, the device includes (iv) a fluidic component including one or more fluidic channels, chambers, pumps, vacuums, and/or valves configured to provide fluidic communication between the sample access component, the sample preprocessing component, and/or the sensor component.

In an embodiment, the device includes microchannels that are arranged to direct the biological sample from the sample access component to the sample pre-processing component, from the sample pre-processing component to the sensor component, and/or from the sensor component to the waste vial. In some embodiments, microchannels are arranged to direct a portion of the biological sample to the fresh sample collection vial.

In an embodiment, the device includes a vacuum system to continually move the biological sample through microchannels. In some embodiments, the vacuum system comprises a vacuum pump and a vacuum tube. In some embodiments, a vacuum system positioned downstream from the site of the sample access component pulls the biological sample into the sample pre-processing component. The described vacuum system may include both active and passive vacuums as understood within the art. The system is sufficient to provide continuous movement of fluid through the system at a near constant velocity and with minimal to no flow interruptions.

(v) Electronic Component

In some embodiments, the device includes (v) an electronic component which may further include one or more components to operate the device, such as a microprocessor, memory, oscillator, power source, and I/O to support integrated peripherals.

The microprocessor may be any microprocessor that can control a plurality of other components of the device. Example microprocessors include, but are not limited to, Raspberry Pi computing equipment, BeagleBone Black computing equipment, Banana Pi computing equipment, PandaBoard computing equipment, LinkSprite pcDuino computing equipment, Intel Galileo Gen 2 computing equipment, Intel NUC series computing equipment, Particle Photon computing equipment, and the like. In an embodiment, the microprocessor is Raspberry Pi. In another embodiment, the microprocessor is BeagleBone Black. In some embodiments, the microprocessor can collect, analyze, and compute data received from the sensor component. In some embodiments, the microprocessor can control components of the fluidic component. In particular such embodiments, the microprocessor engages the vacuum positioned downstream from the sample access component to pull the biological sample into fluidic communication with the device. In some embodiments, the microprocessor has an interface that is capable of measuring the volume of biological sample as it is pulled through the sample access component.

In some embodiments, the electronic component also includes a data communication interface. In some embodiments, the data communication interfaces are wired or wireless interfaces compatible with typical data communication standards, e.g., including, but not limited to Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces. In some embodiments, a user is able to program the device via the interface for data communication. In some embodiments, the data communication interface is able to communicate data including biomarker concentrations to an on-site paramedic through a mobile device. In some embodiments, the data communication interface is able to communicate data including biomarker concentrations to an off-site physician. In some embodiments, the electronic component also includes application specific components including, but not limited to, frequency analysis block, non-volatile memory for storing data, and a liquid measuring block to determine flow quantity.

(vi) Solution Component

In other embodiments, the (vi) solution component includes one or more vials for storage of fluids.

Figure 7:
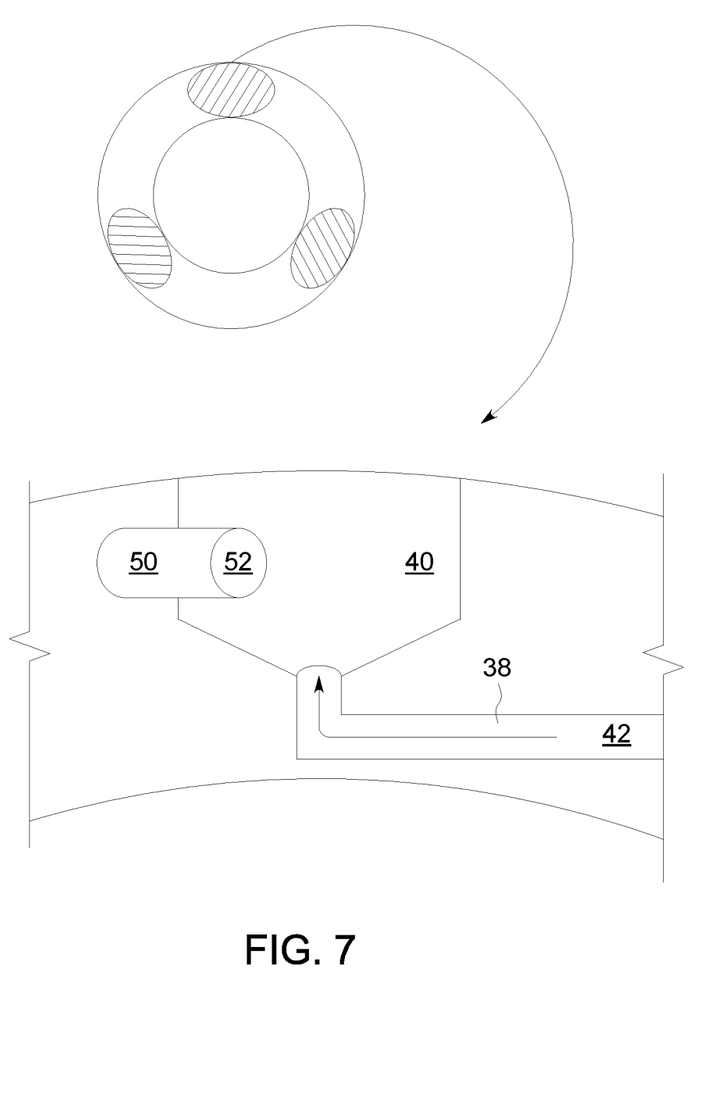
FIG. 7 is a detailed view of a waste collection solution for use with a cuff-like device.

In one embodiment, the solution component includes a waste component. In some embodiments, the waste component includes a waste pipe, vacuum tube, and waste vial, and exemplary embodiment of which is illustrated in FIG. 7.

In another embodiment, the solution component includes a buffer system. In an embodiment, the buffer system comprises a vial which holds a first buffer for dissociating biomarkers and non-target molecules from their corresponding aptamers. Any buffer suitable for dissociation of aptamers from their binding partner may be suitable for use. In an embodiment, the first buffer is ethylenediaminetetraacetic acid (EDTA).

In another embodiment, the buffer system comprises a second vial which holds a second buffer for regenerating the aptamers, thereby allowing for their reuse. Any buffer suitable for regeneration of aptamers as in known in the art may be suitable for use.

In some embodiments, the second buffer is a buffer comprising bivalent metal ions. In some embodiments, the second buffer is an $Mg^{2+}$ containing buffer, an acidic buffer, or a chaotropic buffer. In an embodiment, the second buffer is phosphate-buffered saline (PBS). In yet further embodiments, the device may include any number of additional buffer vials as may be necessary or desired.

In a further embodiment, the solution component includes a waste vial to store used buffer and analyzed interstitial fluid. In yet another embodiment, the solution component includes a fourth vial. In such an embodiment, the solution component comprises a fresh sample collection vial to store fresh biological sample, that is, biological sample that was removed prior to entering the sample pre-processing component. In an embodiment, each of the vials may be removed and replaced.

In yet a further embodiment, the device may include an additional vial of exchange fluid, which may comprise water. When interstitial fluid is removed from the body, this exchange fluid may then be added to the interstitial fluid processed by the device in order to increase the volume of fluid to be analyzed. It is well known that, due to poor hydration, the amount of readily available interstitial fluid available in a particular region of the epidermis may be reduced; in such instances, the interstitial fluid received by the device might not be enough to be read by the machine and therefore analyzed properly. To be clear, and as one of skill in the art will appreciate, the concentration of biomarkers within the interstitial fluid is typically unaffected by low fluid levels in the epidermis. The concentration remains consistent with the body's levels, just the fluid media in which the concentration is suspended by fluctuate or be lowered in such circumstances. By addition of the exchange fluid from the additional vial to the bodily fluid drawn from the subject, the device will be able to obtain better readings and subsequently give more accurate feedback on biomarker concentration. Thus, adding the exchange fluid does not decrease the amount of biomarkers in the interstitial fluid, just enhances its flow. Because it is known that interstitial fluid comprises a large percentage of water, water would be a significant component of the exchange fluid. The exchange fluid may be stored in a vial within the device. It may also be stored within the V-patch (as disclosed above); when interstitial fluid is taken up, the exchange fluid can be added to this already present water. When the V-patch is attached to the device, both the exchange fluid and the interstitial fluid will be taken into the device and analyzed. Alternatively, the V-patch will store the interstitial fluid only, where it is then taken into the device and water (inside the device already) will be mixed with the interstitial fluid and then analyzed.

(vii) Body

In some embodiments, the (vii) body is configured to contain a plurality of other components of the device. In an embodiment, the body is cuff-like as to be worn around a subject's arm or leg. In some embodiments, the body comprises an upper body and a lower body. In some embodiments, the body comprises an interior made in part of flexible materials so as to conform to a subject's arm or leg.

In another embodiment, the body may be ridged with a series of hinges, flexible joints, or multiple adjusters. In some embodiments, the body is molded or created through methods such as 3D printing. In some embodiments, the body may be 1, 2, 3, 4, 5, 6, or 7 inches in length, but alternative embodiments may vary in length. In some embodiments, the inside circumference of the body may be 8, 9, 10, 11, 12, 13, 14, 15, 16, 17, 18, 19, or 20 inches, but alternative embodiments may vary inside circumference. In some embodiments, the body may traverse from a generally open position to a generally closed position. In some embodiments, the body may be a continuous toroidal shape. In some embodiments, the body may comprise at least one adjuster between the upper body and lower body configured to compress and secure the interior region of the body to the subject's arm or leg. In one such embodiment, the adjusters are mating connectors positioned on opposing sides of the cuff. In another such embodiment, the adjuster is a belt and latch which may be adjusted. In yet another such embodiment, the adjuster is an elastic member. In an embodiment, the adjuster has infinite positions such as a toothed strap secured by a ratcheting device that is easy constricted and released by a release mechanism such as a mechanical release button or lever.

Definition

By "about" is meant +/−10% of any recited value.

By "fluidic communication," as used herein, refers to any duct, channel, tube, pipe, reservoir, chamber, or pathway through which a substance, such as a liquid, gas, or solid may pass substantially unrestricted when the pathway is open.

As used herein, "linked" or "linking" is understood to mean attached or bound by covalent bonds, non-covalent bonds, and/or linked via van der Waals forces, hydrogen bonds, and/or other intermolecular forces.

By "biological sample" is meant any specimen obtained from a subject. The biological sample can include any useful material, such as biological (e.g., protein) and/or chemical matter. For example, the biological sample may be blood or interstitial fluid.

By "subject" is meant a human or non-human animal (e.g., a mammal).

By "biomarker" is meant a biochemical characteristic that can be used to diagnose, or to measure the progress of a disease or condition, or the effects of treatment of a disease or condition. A biomarker can be, for example, the presence of a nucleic acid, protein, or antibody associated with the presence of cancer or another disease in an individual. Biomarkers include, but are not limited to, creatinine, troponin 1, alkaline phosphatase, and albumin.

By "non-target molecule" is meant a molecule that is not a biomarker of interest. In particular, a non-target molecule may be a molecule structurally similar to biomarkers of interest.

By "aptamer" is meant ligand-specific oligonucleotide or peptide molecule that can bind to a pre-selected target, such as a protein or peptide, with high affinity and specificity. As would be obvious to the skilled in the art, the term "aptamer" can refer to a plurality of structurally identical aptamers rather than one single aptamer.

Embodiments of the Invention

In one embodiment, as shown in FIGS. 1-2, the invention may be a cuff-like device (10) comprising a body (100) and an adjuster (16). In an embodiment, the body comprises an upper body (11) and a lower body (12) with an interior made in part of flexible materials to conform to a patient's arm or leg. Alternatively, the body may be ridged with a series of hinges, flexible joints, or multiple adjusters. Additionally, the body may be molded or created through other methods such as 3D printing. In one embodiment, the device may be about 3 inches in length with an inside circumference of about 14 inches, but alternative embodiments may vary in size. The body (100) may traverse from a generally open position to generally closed position or may be a continuous toroidal shape. Between the upper and lower body may be an adjuster (16) which is configured to compress and secure the interior region of the cuff to the patient's arm. If the body is made of multiple parts such as a upper body and lower body, then multiple adjusters may be employed on opposing edges, or otherwise as desired. As an example, the adjuster may comprise mating connectors positioned on opposing sides of the cuff, a belt and latch which may be adjusted, or an elastic member. In an embodiment, the adjuster would have infinite positions such as a toothed strap secured by a ratcheting device that is easily constricted and released by a mechanical release button or lever (17, see FIG. 4). FIG. 1 also illustrates an upper interior surface (13) and lower interior surface (14) of the cuff which are each configured to be in direct contact with the patient. A series of microneedles may extend from the lower interior surface. In one embodiment, the microneedles may exist on a removable patch on the lower interior surface of the cuff (or on a V-patch, as previously described). In another embodiment, the microneedles may be positioned below a passage or passages which exist in the body of the cuff and are configured to extend to the surface and into the epidermis. An adhesive, such as EKG adhesive sticker, may be selectively applied to the upper or lower interior area of the cuff to aid in positioning and to prevent radial or axial movement of the cuff once the needles have penetrated the patient. The adhesive sticker may be produced from a base material that stretches such that it may be removed from the device by pulling on the base material to break the adhesive bonds—this approach to remove the adhesive sticker is currently used by 3M® Command Products.

FIG. 2 shows an isometric view of the cuff in a closed position. In an embodiment, the cuff has a user interface (66) on the exterior surface. The user interface (66) may comprise any of the following elements: Graphical display unit, such as an LCD, capable of displaying either text or images; any number of LED which may be used to indicate device state, analysis results, health status of the patient, or other information; switches, knobs, buttons, and other electromechanical input devices which may include controls for device power; Communication and Charging ports configured to connect to external devices and power; additional markings which may be molded into the device made apparent through printing or applied (such as a sticker) which provide instruction or other information such as branding or unit identification numbers.

Also shown on in the exterior surface of the cuff in FIG. 2 are vials (34) for solutions which may aid during analysis. In an embodiment, these vials could be inserted into cavities in the body (100) and secured by mechanical means such as a latch or screw. The vials (34) have a fluid interface (not illustrated) which allows transfer of the fluid from the vials (34) to or from the cuff. The fluid interface may be selectively open or closed by means of electrical controlled value or mechanical valve, passively controlled by a mechanical arrangement such as a check-valve or configured as an open connection such as a tube. Fluids may include solutions for buffering, cleaning, diluting, or the vial may initially be empty and be employed as a receptacle for the collection of waste fluids, bodily fluids, or any other fluids as may be necessary in the operation of the device (10). In one embodiment (such as that shown in exemplary FIG. 5), there can be two vials that both have a generally equivalent volume and whereas vial one (34) contains a EDTA solution and vial two (36) contains a PBS solution; and a third vial (40) which is used for waste collection and sized to receive the contents of vial one, vial two, and the volume of interstitial fluid which is maintained at a 2:2:1 ratio respectively. Each of the vials may be removed for cleaning, refilling, or further analysis as may be necessary.

Figure 3:
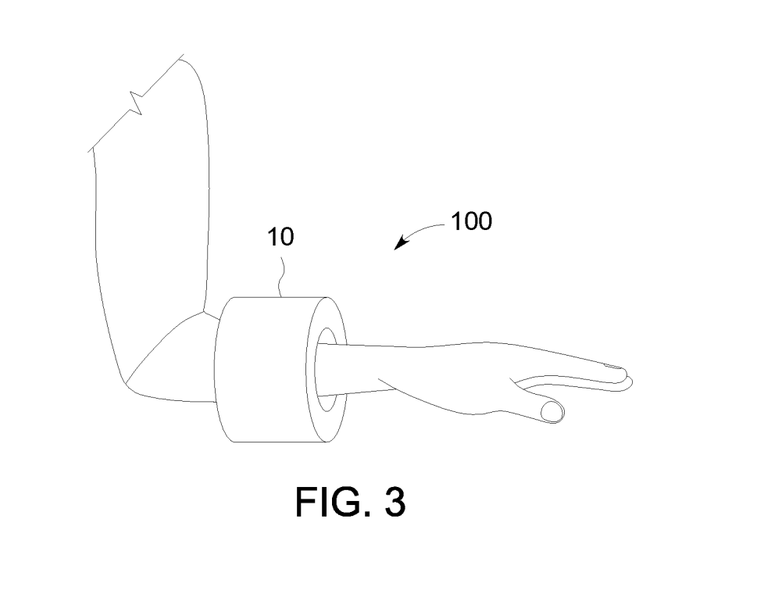
FIG. 3 is a side view of an embodiment of a cuff-like device, shown applied to the forearm of a patient.

FIG. 3 is a side view of the cuff (10) and illustrates how the device may be placed such that the cuff (10) is in communication with the patient's forearm.

Figure 4:
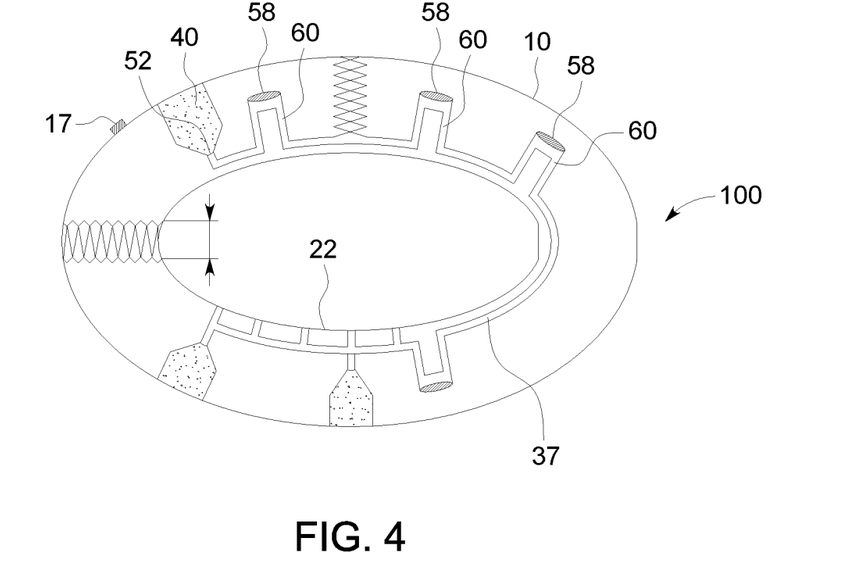
FIG. 4 is a lateral cross-sectional view of an embodiment of a cuff-like device.
Figure 5:
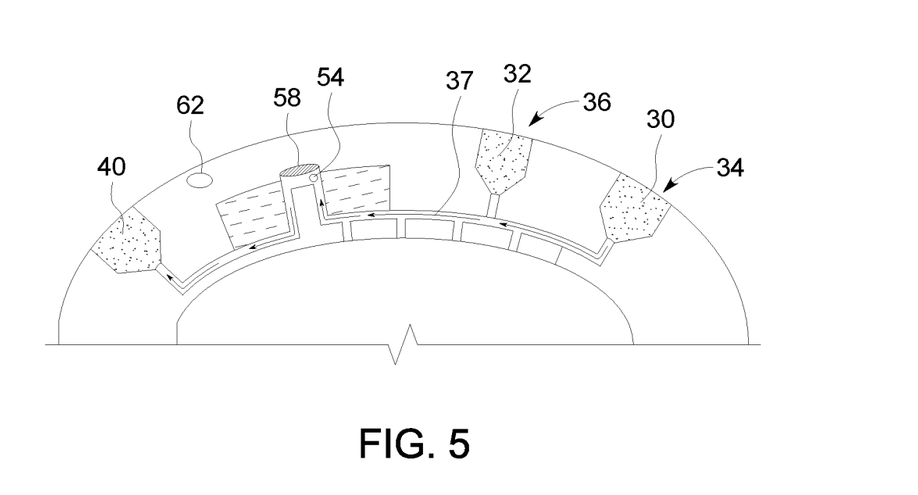
FIG. 5 is a lateral cross-sectional view of an embodiment of a cuff-like device, illustrating the components therein.

A cross-sectional view of the cuff device is shown in FIG. 4 and FIG. 5. An example of device use by a user and internal functionality follows. The lower interior surface (14), which includes a plurality of microneedles (22) is placed on contact with the patient's skin and acted upon with a force (F) directed towards a center-point (C) such that the microneedles will penetrate the skin. Before penetration, and optionally, an adhesive backing may be removed from the upper interior wall (13) of the cuff, opposed to the microneedles (22), exposing an underlying adhesive which secures the device (10) to the patient's skin. In an embodiment the microneedles (22) penetrate the epidermis at an exemplary velocity of 3 meters/second, although other velocities are contemplated and equally within the scope of the invention. The body (100), along with the adjuster (16) are placed such that the body (100) fully encloses the patient's forearm in the interior cavity created by the cuff (10). After the device is secured and the epidermis is penetrated, the process of measurement may begin, as a vacuum positioned downstream from the site of the penetration may be engaged by a microprocessor (62), or other similar electronic mechanism, and the vacuum operates to pull interstitial fluid (56) into a series of channels—such as microchannels (37)—that extend through the interior of the body (100). The microprocessor (62) has an interface that is capable of measuring the volume of interstitial fluid (56) as it is pulled through the system. Examples of the fluid measuring interface could be optical measurement including two sensors disposed across a tube or a mechanical displacement device such as a microturbine. The interstitial fluid (56) is pulled through the microchannels (37) and across a series of quartz crystal plates that have aptamers (54) attached to them, herein called aptamer biosensors, or in an exemplary embodiment, quartz crystal microbalances (58). Each aptamer-based biosensor may be configured to bind with a unique protein molecule. There may be a plurality of aptamer-based biosensors configured to bind with identical protein to allow for a redundant measurement. Once the microprocessor (62) has determined that the desired amount of interstitial fluid (56) has passed across the aptamer-based biosensors, the aptamer-protein binding complex is complete, and the crystal quartz will perform nanoscale weighing by quartz crystal microbalances (58) to determine the protein concentration within the interstitial fluid (56). In one embodiment, there may be 4 crystal quartz microbalances (58) covering most of the diameter of the device and each quartz crystal will have two aptamers (54) of different sequences targeting the same molecule—for a total of eight aptamers (54) wherein a total of four targets may exist in a single cuff (10). In a particular embodiment, the quartz crystal may be about 14 cm in diameter. After the measurement process, the cleansing process will begin, whereby the vacuum will re-engage and EDTA buffer (34) will be released from the first vial and automatically pass through the device to dissociate the target molecule off the aptamers (54) and the combined buffer-protein solution will collect in the waste vial (40). A second PBS buffer (36) will then be released from the second vial and circulate through the device, ultimately collecting in the waste vial (40). While the device is attached, the measurement process as well as the cleansing process may be repeated for multiple cycles for accuracy, error-proofing, or averaging as the need may be. In an embodiment, it may be desired to have 2 mL of each buffer solution for each 1 mL of interstitial fluid.

The electronic system includes the base components necessary for operation: the microprocessor (62), memory, oscillator (64), and necessary I/O to support integrated peripherals. Application specific components are also shown and may include frequency analysis block, non-volatile memory for storing performance data, and a liquid measuring block to determine flow quantity. The electronic system may also include a transceiver for a radio frequency communication such as Bluetooth, Wi-Fi, GSM or other protocol; or wired communication such as a USB or serial port. Furthermore, the microprocessor may obtain location using a GPS receiver. It is envisioned that the device will send results, status, and other information to a receiving device. It is also envisioned that the device will receive information from a transmitting device. For example, a physician will have the ability to adjust settings on the device, including instructing the device to take up biological sample. In yet other examples, a coach may adjust the settings to monitor different biological characteristics relating to an athletic player's continue performance or proneness to injury. Suffice to say, it is contemplated within the scope of the invention that the cuff (10) will not necessarily operate in insolation, but that it may also operate in constant communication with other connected devices over a network (such as via Wi-Fi, the cellular network, GPS, or the like) in order to establish real-time uploading/downloading of data analytics and to convey instructions regarding ongoing biological monitoring.

The frequency analysis block performs the task of detecting the change in resonance frequencies of the quartz crystals before and after sampling. The process of nanoscale weighing is well understood by those in the art and the change in frequency has a linear relationship to the molecules bound to aptamer. By using known values for molecular weight, in relation to the frequencies emitted, algorithms may be employed to know with particular certainty the presence, amount, and concentration of an analyte of interest.

Figure 6:
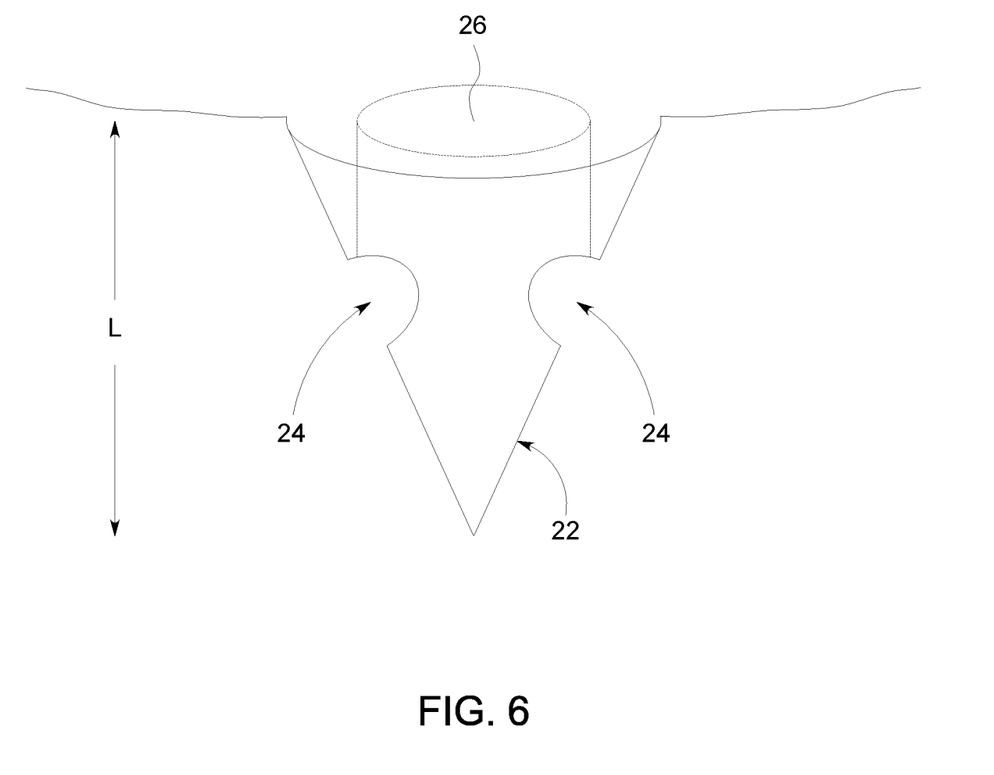
FIG. 6 is a detailed view of an exemplary microneedle.

FIG. 6. shows a close up view of a microneedle (22). The illustrated geometry of the microneedle is generally conical with a closed upper point to pierce the epidermis, and two circular openings on each side of the microneedle (24), which together open into a single hollow base or channel (26). The dual side openings (24) provide redundancy to reduce the occurrence of needle clogging. When a microneedle is clogged, for whatever reason, it can potentially compromise the uptake of interstitial fluid (56) into the device. By improving on the existing hollow needle configuration where the opening is placed on the bottom of the needle, and on opposing sides thereof, it will allow continuous flow of fluid by the microneedle even in the event that one of the microneedle openings (24) becomes clogged. Furthermore, the microneedle holes (24) can be adjusted in manufacturing to eliminate unwanted molecules from entering the device. In an embodiment the microneedles may be between 50 micrometers and 400 micrometers in length (L). They will be long enough to consistently penetrate the corneum lucidum where the interstitial fluid is located, but not so long that they might puncture the underlying dermis, damaging the nerve endings and causing acute pain. The needles may be removed from the cuff, sterilized and reused. They may be made from silicon or other material. They may be present on a V-Patch, and the may work together with optional numbing agent(s), as detailed above.

FIG. 7 shows a detailed view of the waste vial (40). Waste fluid travels downstream through the waste tube or pipe (42). The waste fluid is pulled through by a vacuum system which can comprise a vacuum pump and a vacuum tube (50), which may be the same pump as described above with respect to measurement. The vacuum tube (50) is connected to the waste vial (40) in order to pull fluid into the waste vial (40). An air porous filter (52) located on the waste vial (40) keeps the liquid in the container. In one embodiment, the filter may comprise a liquid porous material with air permeable laminate. In another embodiment the filter (52) may comprise a non-porous base material manufactured with tiny apertures like hospital gowns and bedding such that blood and other liquids may not pass through.

FIG. 8 illustrates an embodiment of the sample pre-processing component, as described in detail herein, in relation to other components of the device. The biological sample (e.g., the interstitial fluid) is accessed through the sample access component (including the needle array) and transported to a channel comprising aptamer-MB (73). The aptamer-MB are magnetic beads that have aptamers attached to them. The aptamer-MB are incorporated with the goal of reducing nonspecific binding in the sensor component by binding and removing non-target molecules (74) with similar structure as the biomarkers to be measured by the sensor component. For example, if the biomarkers of interest are creatinine, troponin 1, alkaline phosphatase, and albumin, the aptamer-MB and aptamer-based filter will be specific for non-target molecules similar in structure to creatinine, troponin 1, alkaline phosphatase, and albumin. The aptamer-MB and aptamer-based filter will remove the non-target molecules from the biological sample. Once the biological sample has been analyzed, buffer (e.g. EDTA buffer) will be released from buffer one vial (34) and proceed through microchannels (37) to dissociate non-target molecules bound to aptamers on the aptamer-MB, the aptamer-based filter, as well as the aptamer-QCM. The non-target molecules will proceed with the buffer through the microchannels (37) into the waste vial (40). Next, buffer (e.g., PBS buffer) will be released from the second vial (36) and proceed through the microchannels (37) to regenerate aptamers on the aptamer-MB, the aptamer-based filter, as well as the aptamer-QCM (58) for reuse. The buffer will proceed through the microchannels (37) into the waste vial (40). Each of these vials may be removed. In one embodiment, the waste vial (40) may be removed and replaced with an empty waste vial. In yet another embodiment, the vials containing the first and second buffer (34/36) may be removed and replenished.

Figure 9:
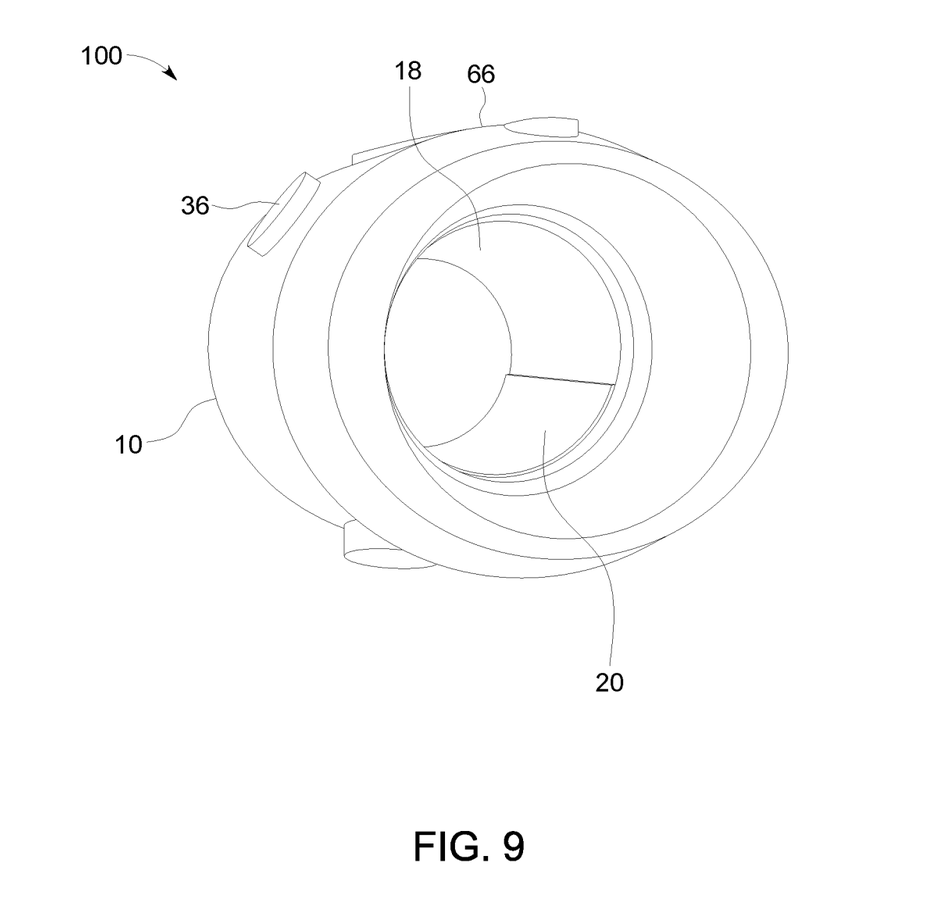
FIG. 9 is an isometric view of an embodiment of a cuff-like device.

FIG. 9 illustrates an isometric view of an embodiment of a cuff-like device (10). As illustrated, the body (100) contains a needle section (20) on a lower interior portion (14), which contains the microneedles (22) as previously described. The upper interior portion (13) contains an adhesive portion (18). The adhesive portion (18) is understood to comprise any known adhesive material that functions to maintain a position of the device (10) and body (100) when it is attached to a subject and the microneedles (22) of the needle portion (20) have punctured the skin of the subject.

In another embodiment, two aptamers (54) specific for the same target biomarker will be used to enhance the accuracy of assaying biomarker concentration. These aptamers will not be randomly clustered on the quartz crystals. In one embodiment, the two different aptamers (54) will be clustered to the same quartz crystal but in separate sections. In another embodiment, the two different aptamers (54) will be clustered to two different quartz crystals. In addition to enhancing the accuracy of protein concentration, allocating the two aptamers (54) to separate locations of the same quartz crystal or separate quartz crystals will enable computational analysis of the binding efficacy of each aptamer (54). For example, if two aptamers (54) specific for troponin 1 are used for determination of protein concentration, each aptamer (54) would have its own section on the quartz crystal or its own quartz crystal that would directly relate to its efficiency in binding troponin 1. If a first aptamer shows a higher troponin 1 concentration in comparison to a second aptamer, it would be possible to assess the efficiency of each aptamer. This would enable continual improvement of biomarker assessment through consistent modification of aptamers used, as well as data rounding and adjustment to ensure accuracy and precision of the measured amounts of analyte.

In another embodiment, the device includes a fourth vial in the solution component that will collect fresh biological sample, that is biological sample that has be accessed by the sample access component but has not reached the sample preprocessing component. This vial with fresh biological sample may be removed from the device using the same method as the other vials. After being removed, the vial and its fresh biological sample may be assessed elsewhere, such as by the stationary device disclosed above, to provide more in-depth physiological assessment. Accordingly, it is envisioned in one embodiment that the device as described herein would be useful for emergent diagnostics and intervention by paramedics, and the fresh biological samples will be used for more comprehensive diagnostics.

In an additional embodiment, the device has a built-in GPS device allowing, for example, a physician to monitor the subject's location en-route to a hospital or treatment facility.

Exemplary in-Field Use (Medical Trauma)

An exemplary method of in-field use of a cuff-like device, specific to medical trauma, is detailed below.

In a first step, the device is engaged to the forearm or leg of a subject/patient and powered on. Microneedles of the device immediately strike the skin of the subject and puncture epidermis deep. A vacuum system within the device activates, the same being turned on by operation of engagement of the microneedles or by communication from a microprocessor of the device, and the vacuum causes the intake of interstitial fluid from the subject. The amount of interstitial fluid may be approximately 1 mL, or some other similar amount. In a further step, the interstitial fluid travels through microchannels within the device with the assistance of the vacuum, the fluid passing through the channels along an interior of the device. A portion of the interstitial fluid may be collected in a pure sample collection vial for later use/testing. The remaining balance of interstitial fluid passes through a channel with aptamer-conjugated magnetic beads and through an aptamer-based filter, wherein non-targeted molecules are selectively removed from the interstitial fluid. In a further step, the filtered interstitial fluid continues through a sensor component comprising a plurality of quartz crystal plates that have aptamers attached to them, wherein biomarkers of interest from the fluid attach to the aptamers. The microprocessor of the device collects, analyzes, and computes data received from the sensor component reflective of the molecular weight, frequency signal, and other data input communicated by the quartz crystal microbalance after the biomarkers of interest have bound to the aptamer.

In a next step, results indicating concentrations of the biomarkers may be sent to both a paramedic on site and a physician (on or off site), such as by Wi-Fi, cellular network, GPS, or by other communicative means. Following the measurement and communication of results, in a next step, EDTA buffer automatically passes through the device, such as from a first vial, and dissociates non-target molecules and biomarkers from the aptamers on the aptamer-conjugated magnetic beads, the aptamer-based filter, and the aptamer-based quartz crystal biosensors. The amount of EDTA buffer solution may be approximately 2 mL, or some other similar amount. The molecules and the waste fluid enter a waste vial. In a next step, PBS solution then passes through the device, such as from a second vial, and regenerates the aptamers on the aptamer-conjugated magnetic beads, the aptamer-based filter, and the aptamer-based quartz crystal biosensors for reuse. The waste fluid enters the waste vial. The measurement and cleansing cycles may optionally each be repeated two or more times, provided that after each measurement cycle, there must be a cleansing cycle to reset the sensor component. After each cycle, the results are automatically sent to both the paramedic and the physician. The pure sample collection vial is removed and stored for later analysis, such as by a separate stationary device that may have the capability of analyzing different or more analytes that may be or may become of interest in the treatment of the patient. The waste vial may be removed from the device, and replaced with an empty waste vial, and the contents therein are disposed with other medical biohazard waste comprising bodily fluids. The vials containing the first and second buffer may be removed and replenished with buffer solution.

In addition to, or together with the above-disclosed method, a removable skin patch, such as a V-patch (previously described) may be utilized to collect interstitial fluid for analysis. In a first step of a method for collecting new or further fluid(s), the V-patch may be provided. In a next step, the V-patch may be unpackaged, altered, engaged, or enabled so as to expose a plurality of microneedles on a substantially flat surface of the V-patch. In a further step, the V-patch may be adhered on the skin of a subject at a desired location, such that contemporaneous with the adhering step, the microneedles will strike the skin of the subject and penetrate the skin to a depth within the epidermis layer (although other embodiments may contemplate different depths for collection of different fluids). In a next step, the V-patch will employ a passive siphon mechanism, using negative pressure or other similar forces, to draw interstitial fluid from the subject through the microneedles and into a collection chamber of the V-patch. The collection chamber may be disposed on a rear portion of the V-patch opposed to the microneedles, such as in back of the microneedles. The collection chamber may hold various amounts of interstitial fluid, such as approximately 1 mL, although other collection amounts and corresponding sizes of collection chambers are contemplated.

In a further step, a user may visually inspect the collection chamber to confirm the desired amount of fluid has been collected therein. In yet a further step, the user may selectively disengage the V-patch from the skin, such as by physically removing the V-patch, at which point the collection of fluid will terminate. The collection chamber may be selectively removable from the V-patch, or it may be integral with the microneedles and therefore comprise one integral unit. In yet a further step, the V-patch (or collection chamber thereof) may be inserted into a stationary analysis device such that the interstitial fluid therein may be analyzed for its contents and the presence (or absence) of certain biomarkers, proteins, or other analytes therein. The methods for analysis could include an aptamer based system, employing the use of quartz crystal microbalances as described herein, or it could employ other methods. Alternatively, in the V-patch may be inserted into a cuff-like device (as previously disclosed) such that the cuff-like device can analyze the fluid from the V-patch in a similar manner as if the cuff-like device had withdrawn the fluid directly from the subject.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excused from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various device components in the embodiments described in this patent document should not be understood as requiring such separation in all embodiments.

For brevity, only a few exemplary implementations are described herein, but other implementations, enhancements and variations, as suggested herein and as would be fully appreciated by one of ordinary skill in the art, can be made based on what is described and illustrated herein.

LIST OF REFERENCE NUMERALS:

| Drawing Number | Term |
| --- | --- |
| 100 | Body |
| 10 | Cuff |
| 11 | Upper Body |
| 12 | Lower Body |
| 13 | Upper Body Interior Surface |
| 14 | Lower Body Interior Surface |
| 16 | Adjuster |
| 17 | Release Mechanism |
| 18 | Adhesive Area |
| 20 | Needle Area |
| 22 | Microneedles |
| 24 | Needle Opening |
| 26 | Needle Channel/Base |
| 28 | Needle Array |
| 30 | Buffer One |
| 32 | Buffer Two |
| 34 | Buffer One Vial |

-continued

| LIST OF REFERENCE NUMERALS: | |
| --- | --- |
| Drawing Number | Term |
| 36 | Buffer Two Vial |
| 37 | Microchannel |
| 38 | Waste Fluid |
| 40 | Waste Vial |
| 42 | Waste Pipe |
| 50 | Vacuum Tube |
| 52 | Waste Filter |
| 54 | Aptamer |
| 56 | Interstitial Fluid |
| 58 | Aptamer-Based Quartz Crystal |
| 60 | Quartz Chamber |
| 62 | Microprocessor |
| 64 | Oscillator |
| 66 | User Interface |
| 68 | Wireless Transmitter |
| 73 | Aptamer-Conjugated Magnetic Beads |
| 74 | Non Targeted Biological sample |
| 75 | Targeted Biological sample |

What is claimed is:

1. A device for detecting and measuring one or more biomarker in a biological sample from a subject, the device comprising:
  a sample access component having at least one microneedle that is adapted to access the biological sample;
  a sample pre-processing component having at least one first aptamer-based magnetic bead conjugate ("aptamer-MB"), the aptamer-MB having a pre-processing aptamer that is specifically configured to chemically bind to non-desired biomarkers, the non-desired biomarkers being different from the one or more biomarker;
  wherein the sample pre-processing component further comprises a pre-processing filter wherein the filter has a pore size that is no larger than the largest biomarker being assessed;
  a sensor component in fluid communication with the sample access component, the sensor component having at least one aptamer that is configured to chemically bind to the one or more biomarker as the biological sample passes through the sensor component, the at least one aptamer being further configured (i) to generate a first resonance frequency prior to being chemically bound to the one or more biomarker and (ii) to generate a second resonance frequency, different from the first resonance frequency, subsequent to being chemically bound to the one or more biomarker; and
  an electronic component that is configured to collect, analyze, and compute data received from the sensor component, such as the first and second resonance frequencies, in order to determine the presence of the one or more biomarker within the biological sample.

2. The device of claim 1, wherein the sensor component further comprises at least one first aptamer-based quartz crystal microbalance ("aptamer-QCM") that contains at least two aptamers for detecting the one or more biomarkers.

3. The device of claim 1, wherein the biological sample is interstitial fluid, and wherein the one or more biomarker is a protein contained within the interstitial fluid.

4. The device of claim 1, wherein the at least one microneedle is elongate along a first axis and axially hollow, and wherein the at least one microneedle has two lateral openings on opposed sides thereof that extend into the axially hollow portion in a direction perpendicular to the first axis.

5. The device of claim 1, wherein the electronic component includes a microprocessor that is configured to calculate the presence and concentration of the one or more biomarker from analyzing the first and second resonance frequencies.

6. The device of claim 5, wherein the electronic component further comprises data communication interfaces that enable the device to communicate remotely with computers or devices regarding the detection and measurement of the one or more biomarker.

7. The device of claim 1, wherein the device is configured as a cuff-like device that may be selectively attached to either one of the arm or leg of the subject.

8. The device of claim 1 further comprising:
  a solution component having at least two vials, the first vial containing a first buffer solution and the second vial containing a second buffer solution that is different than the first buffer solution, the first and second buffer solutions being in selective fluid communication with the sensor component, wherein when at least one of the first and second buffer solutions are selectively put into fluid communication with the sensor component, the at least one buffer solution is configured to chemically dissociate the one or more biomarker from the at least one aptamer.

9. The device of claim 1, wherein the pre-processing filter comprises aptamers configured to bind and remove non-target molecules.

10. The device of claim 2, wherein the sensor component comprises one or more aptamers designated to one or more biomarkers of interest.

11. The device of claim 2, wherein the sensor component comprises two different aptamers designated to each of one or more biomarker of interest.

12. The device of claim 11, wherein the two different aptamers designated to a biomarker of interest are clustered to different sections on the same quartz crystal.

13. The device of claim 11, wherein the two different aptamers are clustered to different quartz crystals.

14. The device of claim 4, wherein the at least one microneedle is equipped with a microneedle filter near the base of the one or more microneedles.

15. The device of claim 14, wherein the microneedle filter comprises a filter mesh configured to selectively obstruct certain molecules by size from entering the interior of the device.

16. The device of claim 6, wherein the electronic component further comprises a GPS receiver.

17. The device of claim 16, wherein the microprocessor is configured to obtain location using a GPS receiver.

* * * * *